United States Patent [19]
Bilder et al.

[11] Patent Number: 5,534,289
[45] Date of Patent: Jul. 9, 1996

[54] STRUCTURAL CRACK MONITORING TECHNIQUE

[75] Inventors: Wayne H. Bilder, Northampton; Richard D. Granata, Bethlehem, both of Pa.; Henry Leidheiser, Jr., Venice, Fla.

[73] Assignee: Competitive Technologies Inc., Bethlehem, Pa.

[21] Appl. No.: 367,039

[22] Filed: Jan. 3, 1995

[51] Int. Cl.$^6$ ........................................................ B05D 3/00
[52] U.S. Cl. .................................................. 427/8; 73/104
[58] Field of Search ................. 73/104, 105; 252/408.1; 427/8, 146, 650

[56] References Cited

U.S. PATENT DOCUMENTS

| | | | |
|---|---|---|---|
| 3,652,225 | 3/1972 | Coffin et al. | 148/273 X |
| 3,803,485 | 4/1974 | Crites et al. | 324/65 R |
| 4,729,742 | 3/1988 | Seitz | 427/150 X |

OTHER PUBLICATIONS

Cheu, Y. F., "Automatic Crack Detection with Computer Vision and Pattern Recognition of Magenetic Particle Indications", *American Society For Nondestructive Testing, Inc.*, Materials Evaluation, 42, Nov. 1984, pp. 1506–1510.

"Eddy Current Imaging Device Offers Prospect of Simple Crack Detection"*Aviation Week & Space Technology*, Jan. 22, 1990, p. 96.

Hopwood, Theodore II, P. E., "Acoustic Emission Inspection of Steel Bridges" *Public Works*, May 1988, pp. 66–69.

Dunker, Kenneth F., Rabbat, Basile G., "Why America's Bridges Are Crumbling"*Scientific American*, Mar. 1993, pp. 66–72.

Kuvin, Brad, F., "Expert Inspection of Steel Bridges", *Welding Design and Fabrication*, Aug. 1988.

"Microencapsulation" *Encyclopedia of Polymer Science And Engineering*, vol. 9, Second Edition, 1987, pp. 724–745.

Pillai, S. A., et al., "Detection and Characterization of Tight Cracks Using Photoelastic Coatings", *The American Society For Nondestructive Testing, Inc.*, Materials Evaluation, Mar. 1992, pp. 367–371.

DeForest, A. V., Ellis, Greer, "Brittle Lacquers as an Aid To Stress Analysis", *Journal of Aeronautical Sciences*, 1940, pp. 205–208.

*Primary Examiner*—Michael Lusignan
*Attorney, Agent, or Firm*—Michael R. Novack

[57] ABSTRACT

A method is disclosed for monitoring a structure for the formation of cracks and for providing protection of the structure from the environment, including the following steps: applying to the structure a first coating comprising microcapsules of a first color, applying over the first coating, a second coating having a second color, and identifying cracked portions which form in the structure by observing changes in the color of the second coating resulting from eruption of microcapsules in the first coating.

6 Claims, 1 Drawing Sheet

STRUCTURAL CRACK MONITORING TECHNIQUE

This invention was made with U.S. government support awarded by the Office of Naval Research, Grant No. NO0014-89-J-1089. The U.S. government has certain rights in this invention.

BACKGROUND

A large portion of the highway infrastructure is in need of repair. Studies indicate that nearly a quarter of the half million highway bridges in the United States have been classified as structurally deficient. Each year, on average, between 150 and 200 spans suffer partial or complete collapse. Current estimates for repairing deficient bridges are of the orders of $100 billion.

The potentially catastrophic consequences of fatigue cracking can be avoided by the early detection of fatigue cracks. Additionally, early detection of cracks can significantly reduce the cost of repairs.

A national mandate requires that bridges be inspected at least every two (2) years. The most frequently used method of inspecting bridge components for fatigue damage has been the elementary method of visual inspection. In order for the inspection to be of any value, the inspectors must find flaws early and accurately judge which ones need immediate repair, and which ones can wait. Although an inspector will typically examine the entire structure, a high percentage of cracks occur in common or "critical" locations. The most revealing sign of a crack is the existence of rust, oxide film and powder. However, since rust does not always appear immediately after a crack is formed, cracks may go undetected during visual inspection.

Once a crack is observed or suspected, the structure is further tested to determine the extent or severity of the damage. A number of techniques are currently used to confirm the existence of a crack. One well-known technique is the application of a dye-penetrant to the crack in question. A liquid penetrant is applied evenly over the surface being tested and allowed to enter open discontinuities. The excess surface penetrant is removed by wiping and the surface is dried. A developer is then applied, drawing the penetrant out of the discontinuity, staining the developer.

Another widely used technique is magnetic particle testing. This test method is used to detect cracks in steel by applying a magnetic field through the surface with a permanent or electromagnet. The specimen is then sprayed with an ink containing fine magnetic dust. The difference in flux density at a crack causes the particles to be attracted to the crack, which makes the crack visible.

Another method, ultrasonic testing, involves the transmission of ultrasonic pulses by piezoelectric transducers through a material. Changes in the amplitude of the received signal indicates the presence of a crack or flaw.

Still another technique, Eddy Current Imaging, measures changes in electrical impedance, produced in a material by an induction coil. A flaw changes the detectable current.

Acoustic emission testing involves the monitoring of transient waves resulting from energy releases due to crack growth.

X-ray and penetrating radiation methods are also used for flaw detection in materials.

Brittle Lacquer coatings have long been recognized as a means for evidencing the existence of strain in a material. These coatings crack in response to the substrate. In order to be of quantitative value, the coating must be used in a controlled environment, and applied in a precise and uniform manner. The lacquer coatings are also limited to work that can be closely observed so that the cracks in the lacquer can be seen. These brittle coatings are of little use for corrosion protection.

Photoelastic coatings are another known crack detection technique. Photoelastic materials, when subject to a stress or strain field, exhibit bifringence, which is seen as a fringe pattern when viewed through a polariscope.

The aforementioned prior art detection techniques require the initial step of observation of a crack by a trained inspector. Additionally, many of these techniques require complex machinery, and/or cumbersome and expensive physical removal of the structural member in question on order to confirm the existence of, or evaluate the extent, of the crack.

Visual inspection of bridge components on site, and at susceptible locations of the structure, remains the first line of action. Thus, there is a current need to improve an inspector's ability to detect cracks during an initial visual inspection. Early detection will result in savings of time and money. Making inspections more accurate will reduce the number of inspections needed, and will minimize repair costs.

Among the objects of the present invention is to provide a method for aiding in the early detection of cracks in a structure. Another object of the present invention is to provide an improved protective coating for structures. A still further object of the invention is to provide a self-activating crack indication system visible to observers with minimal training. A still further object of the present invention is to provide a non-destructive crack indication technique.

SUMMARY OF THE INVENTION

The present invention utilizes microencapsulation to advantage in a crack detection system. Microencapsulation is the envelopment of small solid particles, liquid droplets, or gas bubbles within a coating. Microcapsules are characterized as having a size between 1 and 1000 microns, but can have a wide range of geometries and structures. A microcapsule contains an internal phase, and an outer coating material.

Microcapsule-based products are used in a variety of industries including: pharmaceutical, graphic art, pesticide, and food industries. For instance, in the pharmaceutical industry, microencapsulation provides an effective mechanism for controlled released drugs. The largest application for microcapsules is in the production of carbonless copy paper.

Many processes for preparing microcapsules have been reported in the literature, these techniques include: pan coating, centrifugation, biliquid column, electrostatic encapsulation, vapor deposition, solvent evaporation, and gelation.

Most steel bridges, whether new or reconstructed, are painted. The paint layer applied to the steel structure serves as a protective coating against agents that cause corrosion, which weakens the structure.

Applicant provides a means for simultaneously implementing a crack-detection means, along with the application of a protective coating of paint to a structure. One embodiment of Applicant's method of structural crack monitoring includes the steps of: applying a coating of a first color to the surface of the structure, said coating including microcapsules containing a second color, said microcapsules being subject to breakage upon occurrence of a crack in said structure; and identifying cracked portions of the structure by observing regions of said surface having said second color. As used herein "color" can be any hue, as well as black, white or grey. In another embodiment of Applicant's invention, the a coating of a first color comprising the microcapsules are applied to the structure, and a second coating of a second color is applied over the first coating.

A primary benefit of applicant's method is that the ability to identify a crack is greatly enhanced. Applicant's indication means, which is automatically released when a crack develops, is observable to the unaided eye at a distance of up to thirty feet.

Applicant provides an improved method for the early detection of cracks in a structure by applying a coating formulated with microcapsules, which rupture in response to cracking of the substrate upon which the coating has been applied, indicating the formation of a fracture in the structure. Since the crack can be observed at an early stage, a significant savings in money, and potentially savings of lives, will result. For instance, if a crack is detected at an early stage, a hole can be drilled at the end of the crack to impede the propagation of the crack. Strain gages can then be mounted to the member indicating whether or not the hole is adequately relieving stress. Absent early detection capability, the crack can propagate to a condition that will require replacement of an entire bridge component, such as a girder. Further features and advantages of the invention will become more readily apparent from the following detailed description, when taken in conjunction with the accompanying drawings.

DETAILED DESCRIPTION

Figure 1:
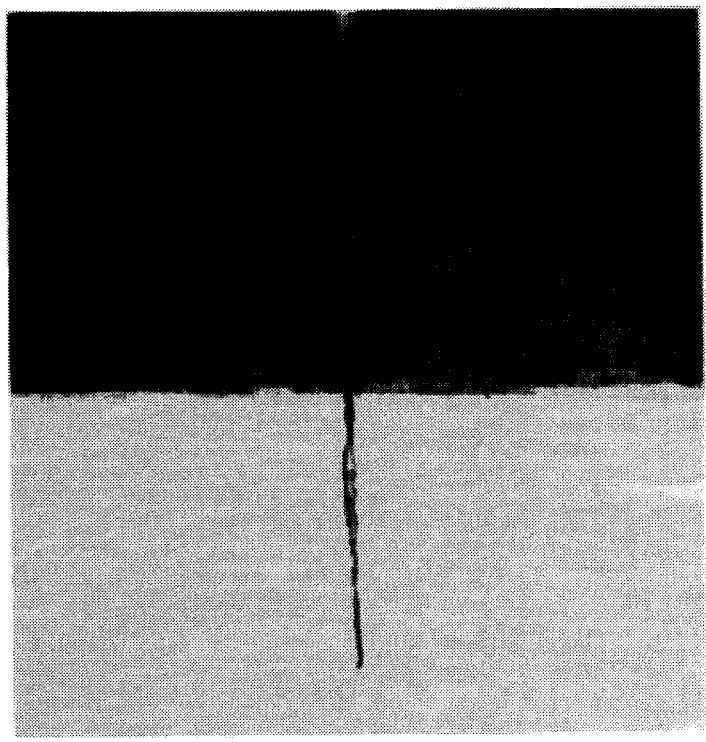
FIG. 1 is a photograph of an epoxy coated steel panel which has been subjected to stress causing a crack in the structure.

FIG. 1 is a photograph of a steel panel which has been subjected to stress causing a crack in the structure. The panel was coated on the bottom half with nitrocellulose lacquer containing microcapsules comprised of an oil-soluble red dye having gelatin walls ranging from 100 to 150 micrometers in diameter. An oil soluble dye is preferable when using an oil-based paint such as a lacquer, since the capsule wall material and the contents should be mutually insoluble, and since the dye and the paint should not degrade the capsule wall from either the inside or outside. If a water based paint is used, the capsule wall would be oil soluble, and the dye water soluble. The Microcapsules were supplied by Thies Technology Inc., St. Louis Mo. The cracked region is indicated by the eruption of the microcapsules.

Figure 2:
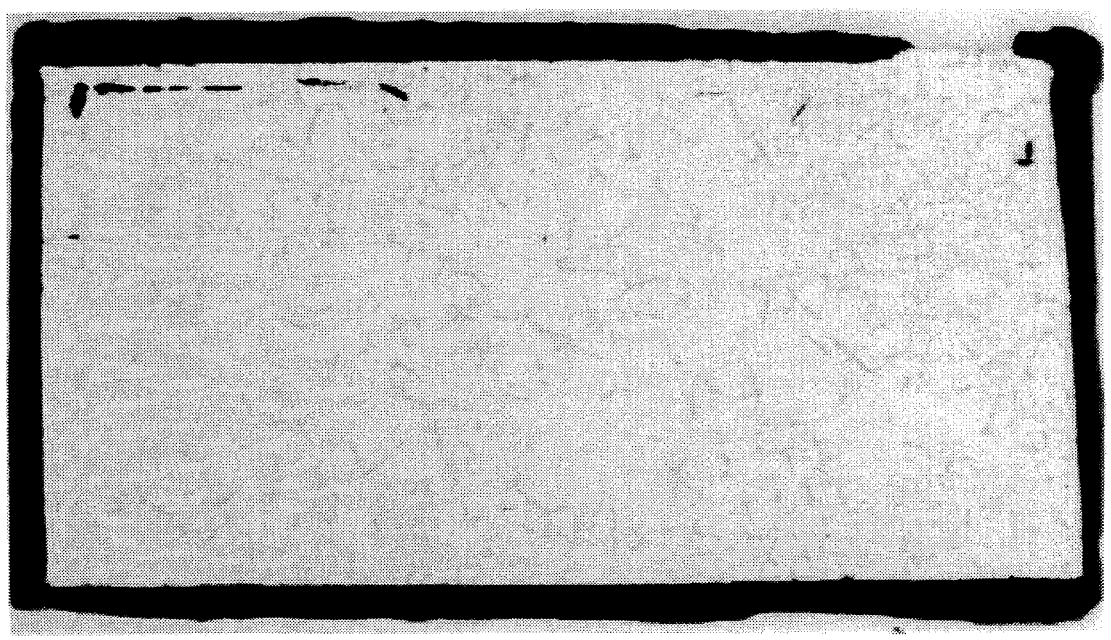
FIG. 2 is a photograph of a nitrocellulose-coated steel panel having the same coating as described in FIG. 1, which has been subjected to a freeze-thaw cycling.

FIG. 2 is a steel panel having the same coating as described in FIG. 1. The steel panel in FIG. 2 has been subjected to a freeze-thaw cycling. No stress forces were applied to the steel panel in FIG. 2. As indicated by the photographs, the crack caused by the stress fracture in FIG. 1, is distinctly different from the cracks resulting from the freeze-thaw cycle. It is also expected that the freeze-thaw cracks can be eliminated by modification of the paint properties.

Additional testing was performed demonstrating the early detection capability of the present invention. The microcapsules used in the experiments, purchased from Thies Technology, Inc, St. Louis Mo., contained an oil-soluble red dye having gelatin walls ranging from 100 to 150 micrometers in diameter. These microcapsules were then mixed with a white nitrocellulose lacquer prior to application. The weight of the dye capsules was 8 to 11% of the paint weight. This coating was then applied to low-alloy steel beams and boxes. Varying stress ranges were then applied to the beams and boxes. In one series of test, I-beams were supported on their ends, and hydraulic presses were used to apply force at strategic locations along the length of the beams. Cracks in the structure, indicated by the presence of released dye from the ruptured microcapsules, were observable to the naked eye when the cracks reached three (3) millimeters in length. Stress continued to be applied to the beam until failure occurred. The cracks were observable as released dye when between 19% and 40% of beam lifetime remained.

The invention has been described with reference to particular embodiments, but variations within the spirit and the scope of the invention will occur to those skilled in the art. For example, it will be understood that suitable microcapsules can be mixed with other types of paints, such as urethane/acrylic, bisphenol-A/epichlorohydrin epoxy, or other paints typically used on structural steel. Also, the wall materials of the microcapsules can be a variety of materials, such as variants of gelatin (gum arabic, polyphosphate, carbooxymethylcellulose, and carragenan), urea formaldehyde, melamine formaldehyde, polyurea, or polyamide. Additionally, it is understood that other colors of dye could be used in the microcapsule. Also, while the invention is particularly applicable to bridges, it can be employed on various other structures, examples being buildings, vehicles or aircraft. Further, a fiber optical light pipe or other optical transfer means can be configured to monitor locations not directly visible to an observer (e.g. visually obstructed areas, physically inaccessible areas, etc.). Also, in some applications, equipment which automatically detects color change could be employed.

We claim:

1. A method for monitoring a structure for the formation of cracks and for providing protection of the structure from the environment, comprising the steps of:

(a) applying to the structure a first coating comprising microcapsules of a first color;

(b) applying over the first coating, a second coating having a second color; and (c) identifying cracked portions which form in the structure by observing changes in the color of the second coating resulting from eruption of microcapsules in the first coating.

2. The method of claim 1, wherein said coating comprises a white nitrocellulose lacquer.

3. The method of claim 2, wherein said microcapsules comprise gelatin walls enveloping an oil soluble dye.

4. The method of claim 3, wherein said gelatin walls have a diameter of between 50 and 250 micrometers.

5. The method of claim 4, wherein the oil soluble dye is red.

6. The method of claim 5, wherein the weight of the microcapsules is between 5% and 20% of the weight of the coating.

* * * * *